United States Patent [19]

Shofu

[11] 4,445,611

[45] May 1, 1984

[54] PACKAGE FOR DENTAL DRILLS AND THE LIKE

[75] Inventor: Koichi Shofu, Marina Del Ray, Calif.

[73] Assignee: Design Applications Incorporated, Marina del Rey, Calif.

[21] Appl. No.: 362,395

[22] Filed: Mar. 26, 1982

[51] Int. Cl.³ ................ B65D 85/24; B65D 6/02; B65D 1/24

[52] U.S. Cl. .................... 206/369; 206/379; 206/380; 206/443; 206/820; 206/45.19; 206/45.34

[58] Field of Search ........... 206/369, 379, 380, 45.34, 206/45.19, 820, 349, 443; 229/40, 9, 19

[56] References Cited

U.S. PATENT DOCUMENTS

| | | | |
|---|---|---|---|
| 2,513,894 | 7/1950 | Rogers | 206/379 |
| 2,530,024 | 11/1950 | Moody | 206/45.34 |
| 2,600,589 | 6/1952 | Swanson | 206/380 |
| 2,842,260 | 7/1958 | Molitor | 206/379 |
| 2,955,705 | 10/1960 | Krueger, Sr. et al. | 220/306 |
| 3,067,864 | 12/1962 | Thompson et al. | 206/369 |
| 3,111,223 | 11/1963 | Jacobi | 229/40 |
| 3,184,054 | 5/1965 | Kuhlman | 206/820 |

Primary Examiner—William T. Dixson, Jr.
Attorney, Agent, or Firm—Keith D. Beecher

[57] ABSTRACT

A package is provided for the marketing and distribution of dental drills, and the like, in which each drill is supported in an upright position in a base, within a rigid casing, and spaced from the walls and top of the casing. The base and casing may be formed of appropriate plastic materials, and the casing may be transparent. A number of like packages may be detachably attached to one another at the edge of their bases in side-by-side relationship, and contained in an open-ended carton. To remove a drill, the package containing the drill is pushed out one end of the carton, and it is detached from the other packages within the carton. The casing is then pulled off the base to expose the drill, and to permit it to be removed.

9 Claims, 5 Drawing Figures

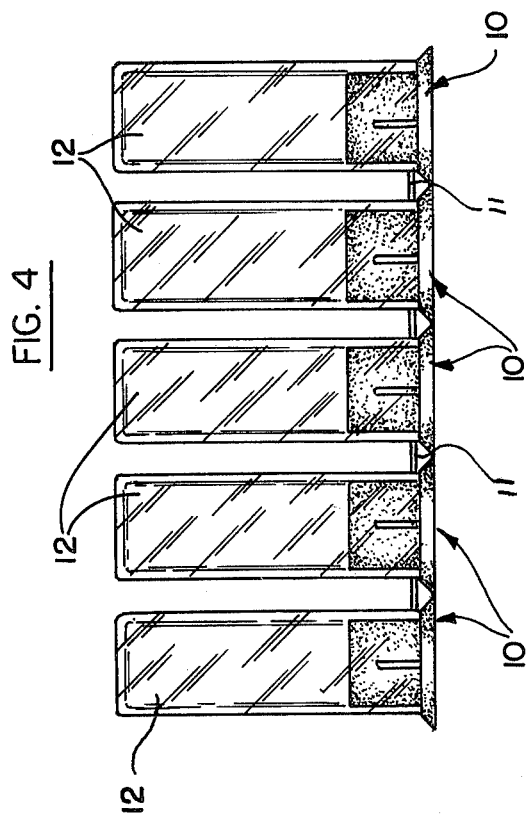
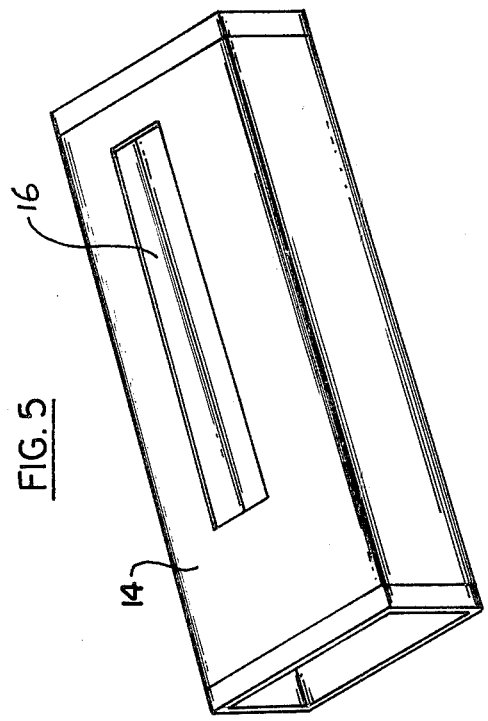
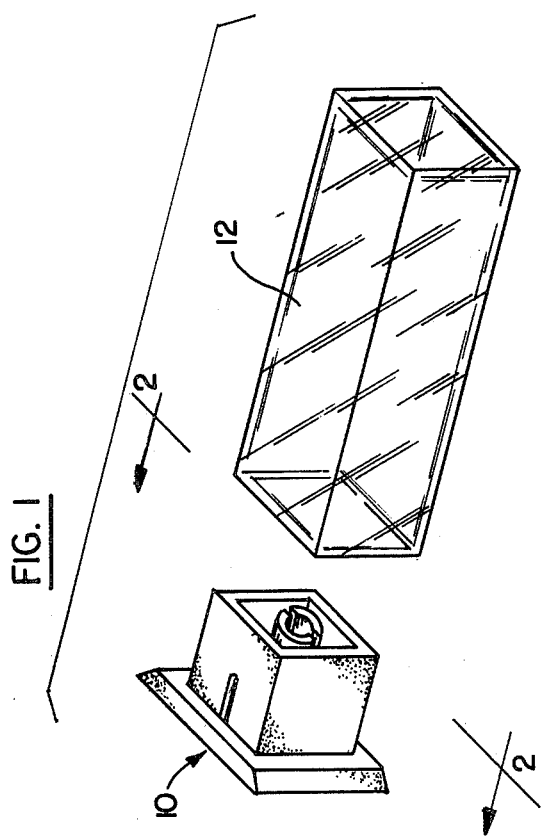
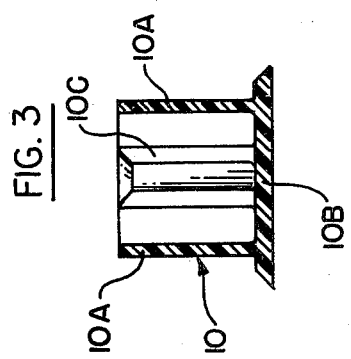
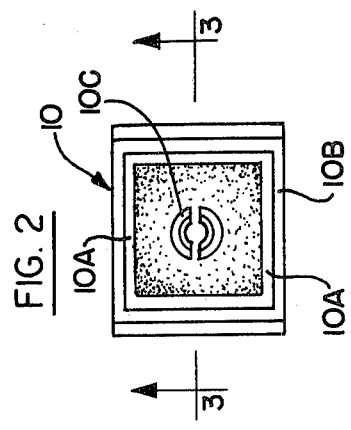

PACKAGE FOR DENTAL DRILLS AND THE LIKE

BACKGROUND

The principal objective of the present invention is to provide a package by which dental drills, or the like, may be conveniently marketed and distributed without damage to the drills, and without injury to persons handling the drills.

BRIEF DESCRIPTION OF THE DRAWING

FIG. 1 is a detached perspective view showing a package constructed in accordance with the invention, and including a base, and a casing, which together constitute the package;

FIG. 2 is a top plan view of the base taken along the line 2—2 of FIG. 1;

FIG. 3 is a side section of the base taken along the line 3—3 of the base;

FIG. 4 is a side view of the package of FIG. 1, and a number of like packages, attached to one another in an aligned relationship, in a manner to permit the individual packages to be detached when desired; and FIG. 5 is a top plan view of an open-ended carton in which the packages of FIG. 4 may be contained.

DETAILED DESCRIPTION OF THE ILLUSTRATED EMBODIMENT

As shown in FIGS. 1, 2 and 3, each of the packages includes a rectangular base 10 which is formed of an appropriate rigid plastic material, and an elongated cover 12 of rectangular section which likewise is composed of an appropriate rigid plastic material, such as an acrylic, and which may be transparent.

The base 10 has side walls 10A which are integral with a bottom 10B, with the bottom extending outwardly from the outer surfaces of the side walls, as shown. An internal socket 10C is formed integral with the bottom 10B, and extends upwardly within the side walls 10A, spaced from the side walls. The socket 10C is split, so that a drill, or similar member, may be inserted into the socket to be supported in the base.

The cover 12 is dimensioned to slip over the outer surface of the side walls 10A of base 10, to be frictionally held in place. The drill supported in the socket 10C is held firmly in the base, and is spaced from the sides and ends of cover 12.

As shown in FIG. 4, a number of packages of the type shown in FIGS. 1-3 may be attached to one another at their bases to be held in an aligned relationship with respect to one another. The bases are detachable, so that the packages may be individually detached from the group, when desired. The covers 12 are also interconnected by a runner 11 for ease of assembly and strength. The runner serves to prevent unwanted separation of the individual packages, and it also enables all the covers to be positioned together on the bases 10, instead of one-by-one.

The packages may be marketed in an open-ended carton 14, shown in FIG. 5, which fits over the aligned packages of FIG. 4 as a sleeve. The carton has a window 16 to display the products. Then, as a package is required, the aligned packages are merely pushed through one end of the carton 14, permitting the end package to be detached from the group and used.

It will be appreciated that while a particular embodiment of the invention has been shown and described, modifications may be made. It is intended in the claims to cover all modifications which come within the true spirit and scope of the invention.

What is claimed is:

1. A package for the distribution of dental drills, and the like, comprising: a rigid base defining an interior space and having at least one side wall and a bottom; a single elongated split socket member mounted on said bottom at the center thereof and extending upwardly in said interior space in spaced relationship with respect to the interior surface of said side wall; and a rigid cover having at least one side wall and a closed end and an open end, said cover having its open end fitted to said base to support said cover in coaxial relationship with said base to form an enclosure for a drill, or the like, mounted in said socket member and extending upwardly from the base into the interior of the cover in spaced relationship with the side wall and closed end of the cover, the open end of said cover extending over the exterior surface of the side wall of said base when said cover is fitted to said base in friction fit therewith.

2. The package defined in claim 1, in which said cover and said base each has four side walls and a rectangular cross-section.

3. The package defined in claim 2, in which the bottom of said base extends outwardly from the external surfaces of the side walls thereof.

4. The package defined in claim 2, in which said base and said cover are each formed of a plastic material, in which the closed end and side walls of the cover are integral with one another, and in which the side walls of the base, and the bottom thereof and the socket member are all integral with one another.

5. The package defined in claim 4, in which said cover is formed of a transparent plastic material.

6. The package defined in claim 4, and which includes a plurality of like packages aligned with respect to one another and each having its base detachably attached to the base of an adjacent package, with the bottoms of the bases positioned in coplanar relationship with respect to one another.

7. The package defined in claim 6, and which includes a runner detachably interconnecting the covers to one another.

8. The package defined in claim 6, and which also includes an open-ended carton for receiving the aligned packages and serving as a protective sleeve therefor.

9. The package defined in claim 8, in which said carton has a transparent window formed therein.

* * * * *